United States Patent
Derenzo et al.

(10) Patent No.: US 9,170,242 B2
(45) Date of Patent: Oct. 27, 2015

(54) LIQUID CHROMATOGRAPHY DETECTION UNIT, SYSTEM, AND METHOD

(75) Inventors: Stephen E. Derenzo, Pinole, CA (US); William W. Moses, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 633 days.

(21) Appl. No.: 13/391,725

(22) PCT Filed: Aug. 24, 2010

(86) PCT No.: PCT/US2010/046556
§ 371 (c)(1), (2), (4) Date: Mar. 27, 2012

(87) PCT Pub. No.: WO2011/028552
PCT Pub. Date: Mar. 10, 2011

(65) Prior Publication Data
US 2012/0176614 A1    Jul. 12, 2012

Related U.S. Application Data

(60) Provisional application No. 61/236,421, filed on Aug. 24, 2009.

(51) Int. Cl.
*G01N 30/62* (2006.01)
*G01N 30/00* (2006.01)

(52) U.S. Cl.
CPC ............ *G01N 30/62* (2013.01); *G01N 2030/77* (2013.01)

(58) Field of Classification Search
CPC ........................... G01N 30/62; G01N 2030/77
USPC ................. 210/635, 656, 96.1, 198.2; 422/70
See application file for complete search history.

(56) References Cited

U.S. PATENT DOCUMENTS

| | | | |
|---|---|---|---|
| 2004/0071631 A1* | 4/2004 | Daghighian | 424/1.11 |
| 2004/0129886 A1* | 7/2004 | Lecoq | 250/363.03 |
| 2008/0064110 A1* | 3/2008 | Elizarov et al. | 436/50 |
| 2009/0000358 A1* | 1/2009 | Kerkdijk | 73/61.55 |
| 2011/0196234 A1* | 8/2011 | Buono et al. | 600/436 |

OTHER PUBLICATIONS

Takei 'Sensitive measurement of positron emitters eluted from HPLC' Applied Radiation and Isotopes (Applied Radiation and Isotopes 55 (2001) 229-234).*
Huber et al. 'Development of a High-Sensitivity Radiation Detector for Chromatography' 2009 IEEE Nuclear Science Symposium Conference Record (Oct. 2009) p. 2620-2624.*

* cited by examiner

*Primary Examiner* — Ernest G Therkorn
(74) *Attorney, Agent, or Firm* — Lawrence Berkeley National Laboratory (57) ABSTRACT

An embodiment of a liquid chromatography detection unit includes a fluid channel and a radiation detector. The radiation detector is operable to image a distribution of a radiolabeled compound as the distribution travels along the fluid channel. An embodiment of a liquid chromatography system includes an injector, a separation column, and a radiation detector. The injector is operable to inject a sample that includes a radiolabeled compound into a solvent stream. The position sensitive radiation detector is operable to image a distribution of the radiolabeled compound as the distribution travels along a fluid channel. An embodiment of a method of liquid chromatography includes injecting a sample that comprises radiolabeled compounds into a solvent. The radiolabeled compounds are then separated. A position sensitive radiation detector is employed to image distributions of the radiolabeled compounds as the radiolabeled compounds travel along a fluid channel.

14 Claims, 12 Drawing Sheets

LIQUID CHROMATOGRAPHY DETECTION UNIT, SYSTEM, AND METHOD

RELATED PATENT APPLICATIONS

This application is the 371 national phase application of International application number PCT/US2010/046556, filed Aug. 24, 2010, which claims priority to and the benefit of U.S. Provisional Application No. 61/236,421, filed on Aug. 24, 2009, which is hereby incorporated by reference in its entirety.

STATEMENT OF GOVERNMENTAL SUPPORT

This invention was made with government support under Contract No. DE-AC02-05CH11231 awarded by the U.S. Department of Energy. The government has certain rights in this invention.

BACKGROUND OF THE INVENTION

The present invention relates to the field of liquid chromatography and, more particularly, to the field of liquid chromatography of radiolabeled compounds.

High Performance Liquid Chromatography (HPLC), or high pressure liquid chromatography as it is sometimes referred, is used to analyze a mixture of organic compounds and identify the individual components. In this technique a multi-component solution is introduced into a stream of solvent (mobile phase) flowing over a stationary phase (contained in a tubular column). Separation of different compounds results from differences in their relative affinity for the stationary and mobile phases. Usually the separated compounds are detected using infra-red or ultra-violet sensors at the exit of the column. This is a satisfactory technique for analyzing the molecular content of biological systems, but is less affective in measuring the turnover of molecules that occur during metabolic processes. For turnover measurements, a radioactive molecule is introduced to the biological system and any metabolic products resulting from reactions of the initial molecule will be radioactive also. The metabolic products of such reactions may be referred to as radiolabeled compounds. In this application, a radiation detector is placed at the exit of the column to detect the radiolabeled compounds. Many HPLC studies in biochemistry use short-lived radiotracers, with increased sensitivity being especially important because some radiolabeled compounds are present only in low concentrations, such as intermediate metabolites.

A typical HPLC radiation detector system includes a reservoir, a pump, an injector, a separation column, and a detector, which are connected in series by tubing. The reservoir contains a solvent that is continuously pumped through the column and the detector. The injector mixes the sample to be analyzed with a small amount of solvent and injects this solution into the solvent stream. As the sample passes through the separation column the various components separate due to the differences in their transport velocity and individual compounds exit the column at different times. The properties of the column are chosen for optimal separation of the compounds of interest. Small-diameter tubing carries the compound (and solvent) from the exit of the column into a detector that uses some attribute of the compound (such as its optical absorbance) to measure the relative concentration of the compound as a function of time. Assuming that the column has separated the individual compounds, each compound will be seen as a single peak in the detector output. The separation between peaks is determined by the properties of the column, solvent, compound, and pumping speed, but typically ranges from a few seconds to minutes. The width of each peak depends on these same properties, but is typically a few seconds. The ratio of the peak width to separation determines the ability to resolve the individual peaks (i.e., the compounds).

The area of each peak is proportional to the amount of the corresponding compound in the sample. A sensitive detector with good signal-to-noise ratio is desired to accurately measure small concentrations of the compounds. In practice, radiolabeled compounds and a radiation detector provide one of the most sensitive means of performing HPLC. The radiation detector is typically a piece of CsI:Tl scintillator crystal coupled to a PIN photodiode read out in current mode. The detector is placed in close proximity to the tubing, and lead shielding is placed outside of the detector/tubing. Although the volume of tubing observed by the radiation detector is small (typically 0.75 mm diameter and ~6 cm long), the sensitivity of the detector is sufficient for many applications. For applications where higher sensitivity is desired, the tubing is coiled around the detector. This increases the length of time that the peak spends near the detector by a factor of n, where n is the number of turns of tubing, and so increases the sensitivity by a factor of n. However, increasing the length of time that the peak spends near the detector can also increase the measured width of the peak and so degrade the ability to separate peaks.

As an example, consider the performance for the conventional radiation detector in the case of a compound whose peak width is 5 seconds at the exit of the column, the solution is pumped through the system at a rate of 1 mL/minute, and the tubing is 0.75 mm diameter. In this case the liquid flows through the tubing at 3.65 cm/sec. The sensitivity of the system will be proportional to the length of time each volume element of the liquid spends in close proximity to the detector, but the width of the peak is blurred by the same amount. If the conventional radiation detector is 2 cm diameter, and if n loops of tubing are placed around its diameter, each volume element of the liquid will spend 1.7n seconds near the detector. For five loops, the detection time is 8.5 seconds, which will broaden the apparent width of the peak from 5 seconds to 10 seconds. For a $^{11}$C radiolabeled compound (half-life=20.38 minutes, mean life 29.4 minutes) with a 10 minute residence time in the HPLC column and a measurement time of 8.5 seconds (0.14 minutes), the fraction f of disintegrations that will occur near the detector is given by $f=\exp(-10/29.4)*[1-\exp(-0.1.4/29.4)]=0.0034$. It would be desirable to improve the detection fraction f.

SUMMARY OF THE INVENTION

Embodiments of the present invention include a liquid chromatography detection unit, a liquid chromatography system, and a method of liquid chromatography. An embodiment of a liquid chromatography detection unit includes a fluid channel and a position sensitive radiation detector coupled to the fluid channel. The position sensitive radiation detector is operable to image a distribution of a radiolabeled compound as the distribution travels along the fluid channel.

An embodiment of a liquid chromatography system includes an injector, a separation column, and a position sensitive radiation detector. The injector is operable to inject a sample that includes a radiolabeled compound into a solvent stream. The separation column is coupled to the injector. The position sensitive radiation detector is coupled to the separation column and is operable to image a distribution of the radiolabeled compound as the distribution travels along a fluid channel.

An embodiment of a method of liquid chromatography includes injecting a sample that comprises first and second radiolabeled compounds into a solvent. The first and second radiolabeled compounds are then separated. A position sensitive radiation detector is employed to image distributions of the first and second radiolabeled compounds as the radiolabeled compounds travel along a fluid channel.

BRIEF DESCRIPTION OF THE DRAWINGS

The present invention is described with respect to particular exemplary embodiments thereof and reference is accordingly made to the drawings in which:

FIGS. 10a and 10b provide experimental results for an injection of 381 µCi [$^{11}$C]carfentanil into an experimental setup of a liquid chromatography system of the present invention.

FIGS. 11a and 11b provide experimental results for an injection of 2.5 µCi [$^{11}$C]carfentanil into an experimental setup of a liquid chromatography system of the present invention.

FIGS. 12a and 12b provide experimental results for an injection of about 1 µCi [$^{11}$C]methyl iodide into an experimental setup of a liquid chromatography system of the present invention.

DETAILED DESCRIPTION

Embodiments of the present invention include a liquid chromatography detection unit, a liquid chromatography system, and a method of liquid chromatography. As used herein, the term "liquid chromatography" includes HPLC (high performance or high pressure liquid chromatography).

Figure 1:
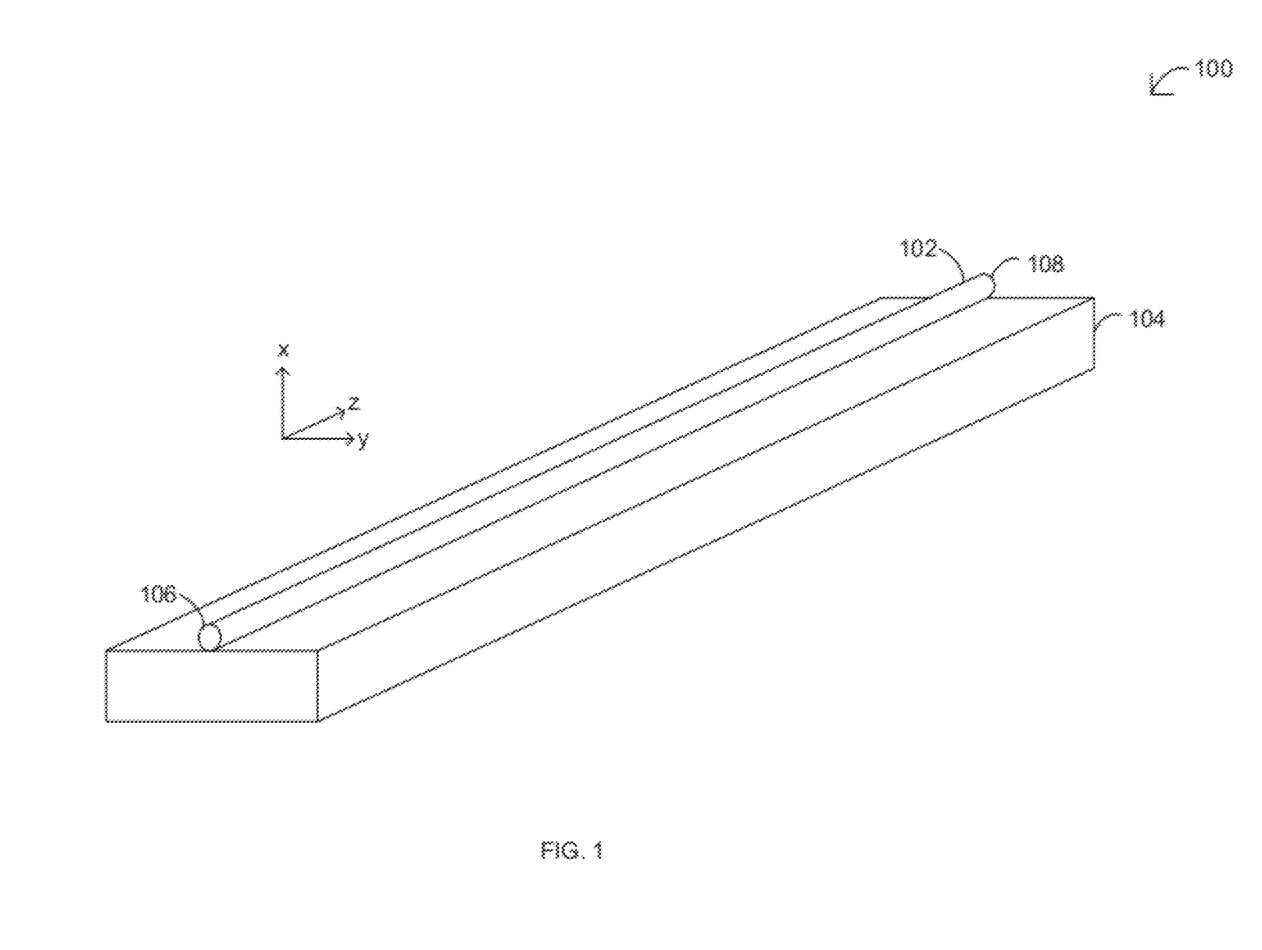
FIG. 1 illustrates an embodiment of a liquid chromatography detection unit of the present invention.
Figure 2A:
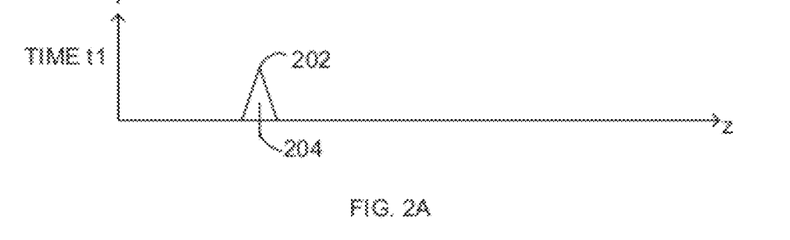
FIGS. 2A, 2B, 2C, and 2D graphically illustrate an operation of a liquid chromatography detection unit in accordance with an embodiment of the present invention.
Figure 2B:
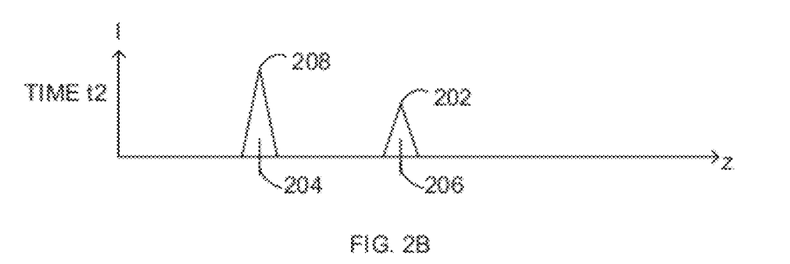
Figure 2C:
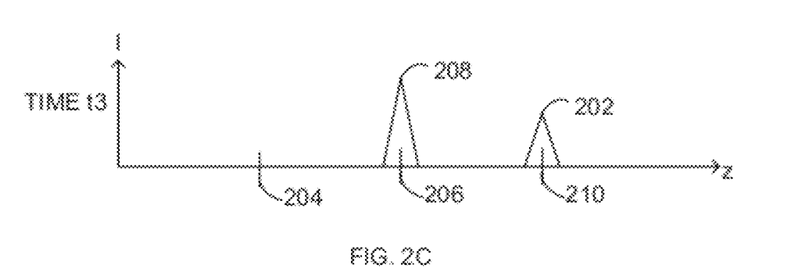
Figure 2D:
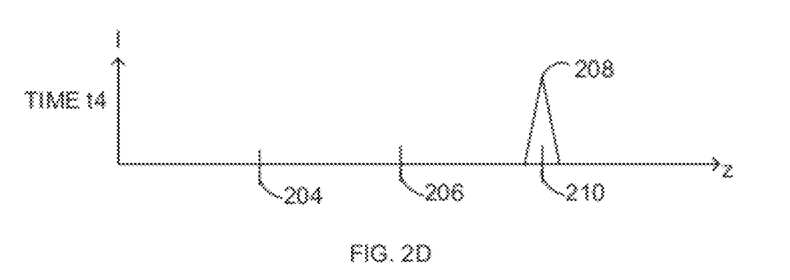

An embodiment of a liquid chromatography detection unit of the present invention is illustrated in FIG. 1. The detection unit 100 includes a fluid channel 102 and a position sensitive radiation detector 104. In an embodiment, the fluid channel 102 comprises tubing. The radiation detector 104 is in close proximity to the fluid channel 102. For example, the fluid channel 102 may be attached to the radiation detector 104 or the fluid channel 102 may be coupled to the radiation detector 104 by way of a support structure (not shown). In an embodiment, the radiation detector 104 comprises a gamma camera. In other embodiments, the radiation detector 104 comprises a PET camera (see below) or some other suitable position sensitive radiation detector. In operation, a radiolabeled compound enters the fluid channel 102 at a first end 106, travels along the fluid channel 102, and exits the fluid channel 102 at a second end 108. During such an operation, the radiation detector 104 images a distribution of a radiation intensity produced by the radiolabeled compound as it travels along the fluid channel 102. In an embodiment, the radiation produced by the radiolabeled compound comprises positron emission, in which a positron may be detected by detecting a pair of gamma rays produced by annihilation of the positron. In another embodiment, the radiation produced by the radiolabeled compound comprises gamma rays produced by nuclear emission. As depicted in FIG. 1, the z-direction is in the direction of fluid flow and the x- and y-directions are orthogonal to the fluid flow.

An operation of the liquid chromatography detection unit 100 is illustrated graphically in FIGS. 2A, 2B, 2C, and 2D. These charts provide distributions of radiation intensity (I) along the length "z" of the liquid chromatography detection unit 100 at particular points in time, $t_1$, $t_2$, $t_3$, and $t_4$, respectively. At time $t_1$, a distribution 202 of a first radiolabeled compound sufficiently travels along the fluid channel 102 such that the radiation detector 104 images the distribution 202 at position 204. Between time $t_1$ and time $t_2$, the distribution 202 travels along the fluid channel 102 to position 206 and a second distribution 208 of a second radiolabeled compound arrives at position 204, which are both imaged by the radiation detector 104. Between time $t_2$ and time $t_3$, the distributions 202 and 208 travel along the fluid channel 102 to positions 206 and 210, respectively, where the distributions 202 and 208 are imaged by the radiation detector 104. Between time $t_3$ and time $t_4$, the distribution 202 passes out of view of the radiation detector 104 and the distribution 208 travels along the fluid channel 102 to position 210, where it is imaged by the radiation detector 104. A data acquisition unit (not shown) may be used to combine the three images for the distribution 202 and the three images for the second distribution 208 to produce more accurate images of the distributions 202 and 208. These more accurate images may be used to produce more sensitive determinations of the concentrations of the first and second radiolabeled compounds, respectively.

It will be readily apparent to one skilled in the art that many more images may be produced of the distributions 202 and 208 by the radiation detector 104 as they travel along the fluid channel 102, which may be used to produce even more sensitive determinations of the concentrations of the first and second radiolabeled compounds, respectively. In effect, such an operation produces a "movie" of the distributions 202 and 208 as they pass through the fluid channel 102.

Figure 3:
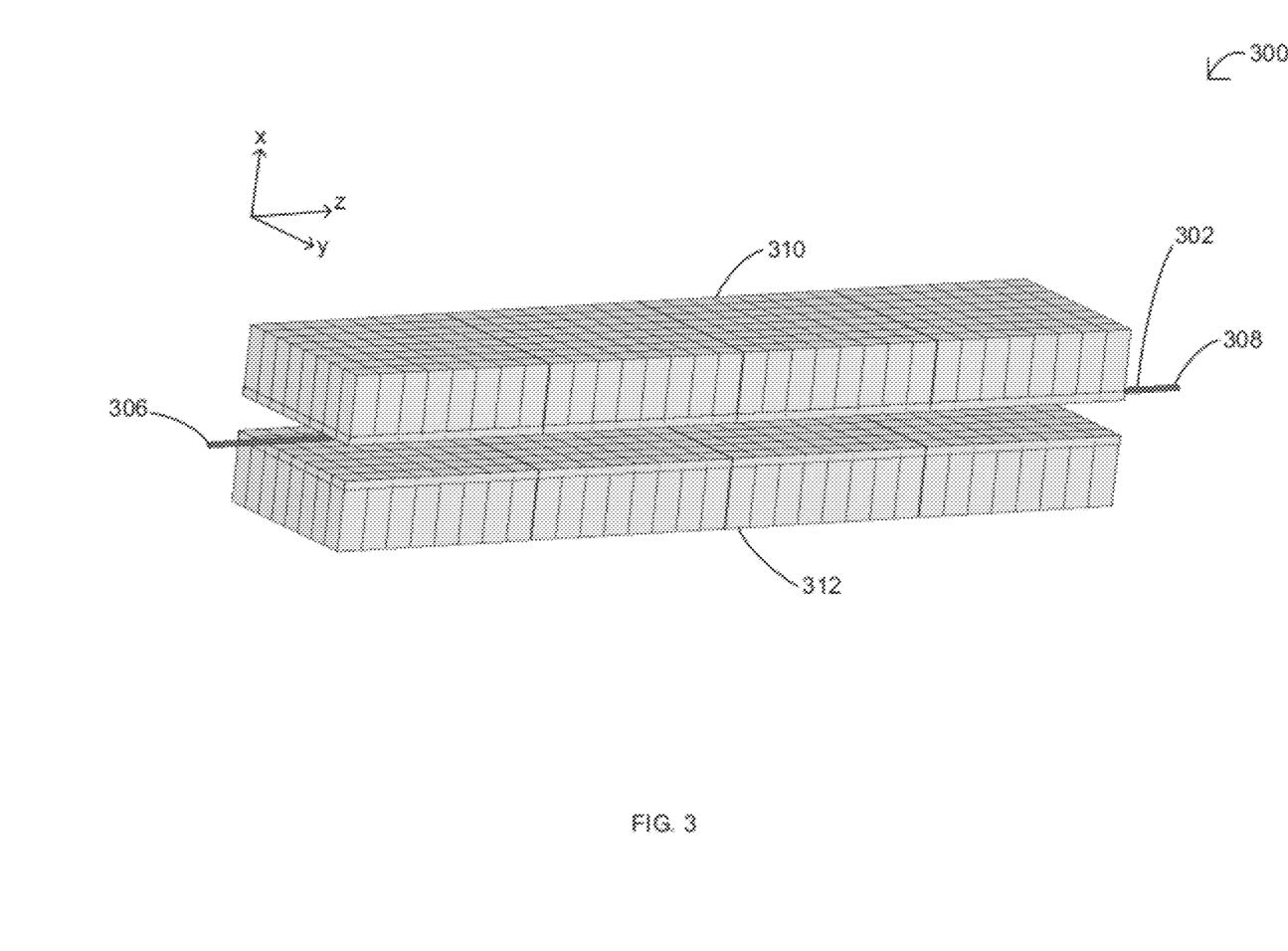
FIG. 3 illustrates an embodiment of a liquid chromatography detection unit of the present invention.

An embodiment of a liquid chromatography detection unit of the present invention is illustrated in FIG. 3. The liquid chromatography detection unit 300 includes a fluid channel 302 and a PET (positron emission tomography) camera 304. The fluid channel 302 is coupled to the PET camera 304, for example, by a support structure (not shown). In an embodiment, the fluid channel 302 comprises tubing parallel to the z-axis, for example, 0.75 mm diameter tubing. In an embodiment, the PET camera 304 is a parallel plane PET camera that includes first and second planar PET detector modules, 310 and 312. In operation, a radiolabeled compound enters the fluid channel 302 at a first end 306, travels along the fluid channel 302, and exits the fluid channel 302 at a second end 308 while the PET camera 304 images a distribution of a radiation intensity produced by the radiolabeled compound over time as the radiolabeled compound travels along the fluid channel 302.

In an embodiment, a positron is produced by radioactive decay of a positron emitting isotope (e.g., $^{11}$C). The positron is annihilated when it combines with an electron, which produces a pair of back-to-back gamma rays. The first gamma ray is detected by the first PET detector module 310 and the second gamma ray is detected by the second PET detector module 312. The first and second PET detector modules. 310 and 312, detect the first and second gamma rays, respectively, as coincident gamma rays (i.e. the modules 310 and 312 detect the gamma rays arriving simultaneously). A mid-point of a line between first and second detection points on the modules 310 and 312 determines a point in space at about where the positron emission occurred.

Figure 4:
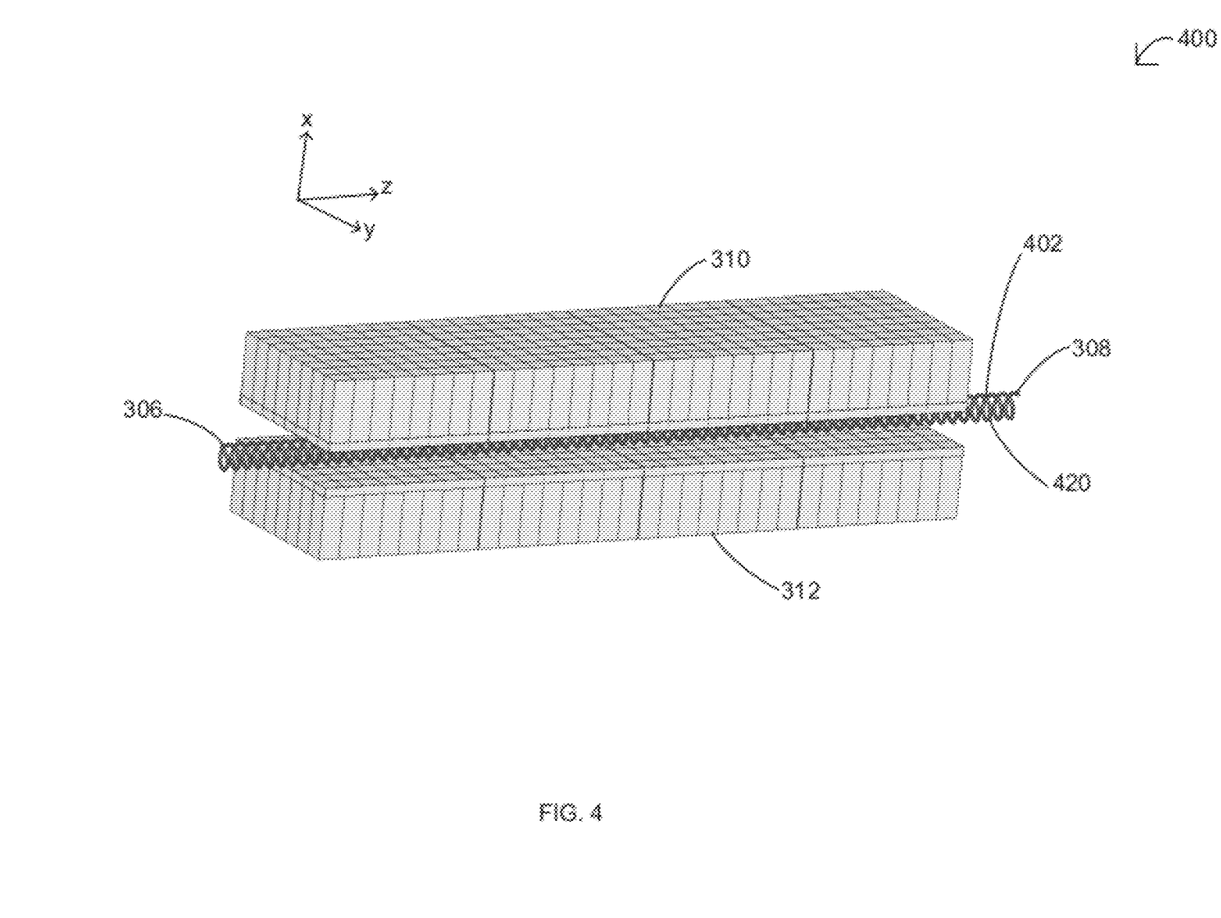
FIG. 4 illustrates an embodiment of a liquid chromatography detection unit of the present invention.

An embodiment of a liquid chromatography detection unit of the present invention is illustrated in FIG. 4. In the liquid chromatography detection unit 400, the fluid channel 302 of the detection unit 300 (FIG. 3) is replaced with a fluid channel 402 that is arranged in a helix 420, which results in a longer transit time of a radiolabeled compound through the detection unit 400 compared to the detection unit 300. In other words, the helix 420 produces an effective velocity through the detection unit 400 that is significantly lower than the velocity in the detection unit 300. The longer transit time allows more sensitive imaging of the distribution of the radiation intensity produced by the radiolabeled compound. In an embodiment, the distribution of radiation intensity is determined along the z-axis without regard to the positions of the radiation intensity in the x- and y-directions. In another embodiment, the distribution of the radiation intensity is determined with respect to the x-, y-, and z-directions.

Figure 5:
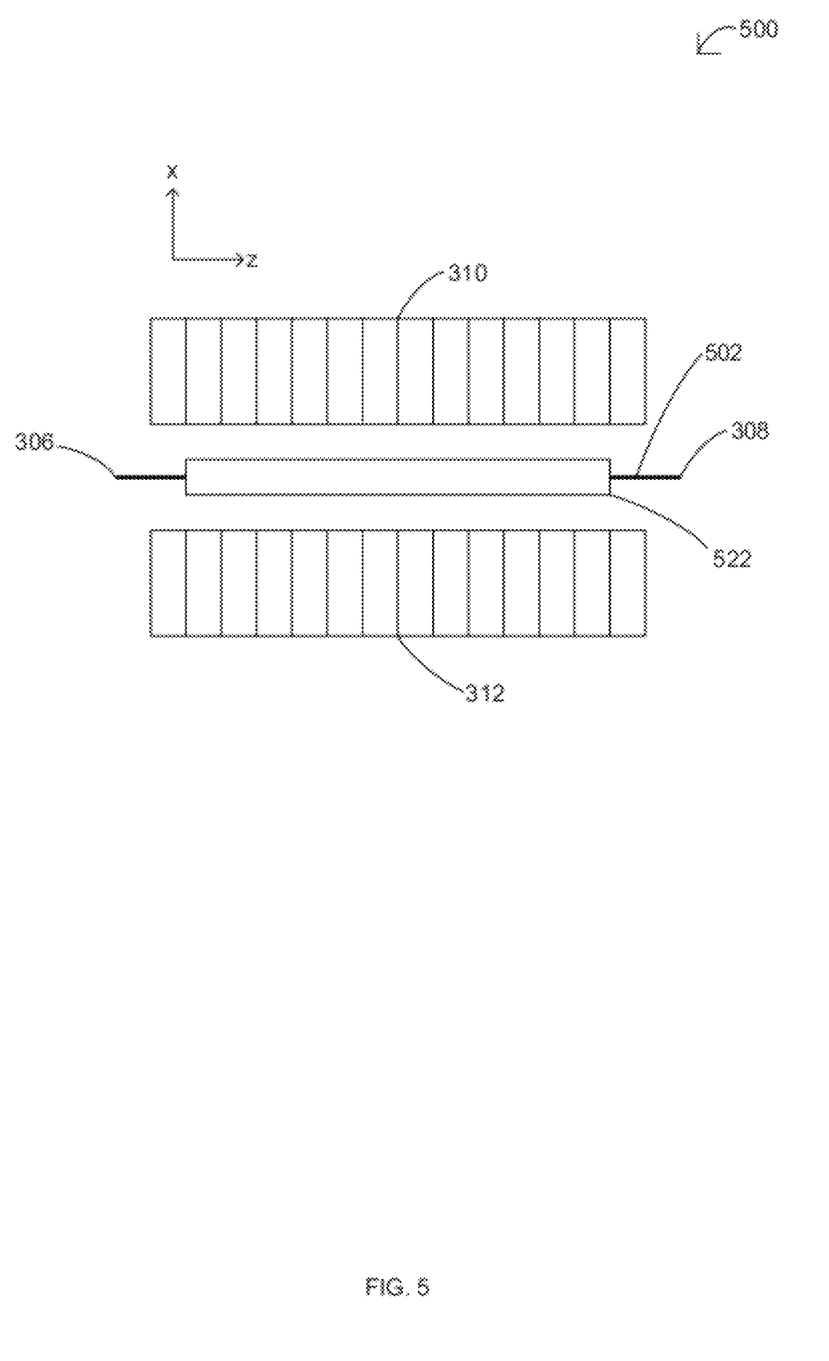
FIG. 5 illustrates an embodiment of a liquid chromatography detection unit of the present invention.

Another embodiment of a liquid chromatography unit of the present invention is illustrated in FIG. 5. In the liquid chromatography detection unit 500, the fluid channel 302 of the detection unit 300 (FIG. 3) is replaced with a fluid channel 502 that includes a separation column 522. The separation column 522 provides a slower transit time of a radiolabeled compound through the detection unit 500 compared to the detection unit 300 (FIG. 3) or the detection unit 400 (FIG. 4). In an embodiment, the solution to be analyzed enters the separation column 522 with two radiolabeled compounds that are not separated and imaging of distributions of radiation intensity produced by the two compounds begins when differences in transport velocities of the two compounds causes them to separate sufficiently.

It will be readily apparent to one skilled in the art that in the liquid chromatography unit 500, the fluid channel can comprise a plurality of separation columns. For example, the separation column 522 may be replaced with two separation columns coupled together. Further, it will be readily apparent to one skilled in the art that the separation column 522 may extend beyond the first end 306 so that radiolabeled compounds may separate before entering a view of the PET camera 304. Moreover, it will be readily apparent to one skilled in the art that a pre-separation column (not shown) may be coupled to the separation column 522 upstream of the first end 306 so that the radiolabeled compounds separate prior to entering the separation column 522.

Figure 6:
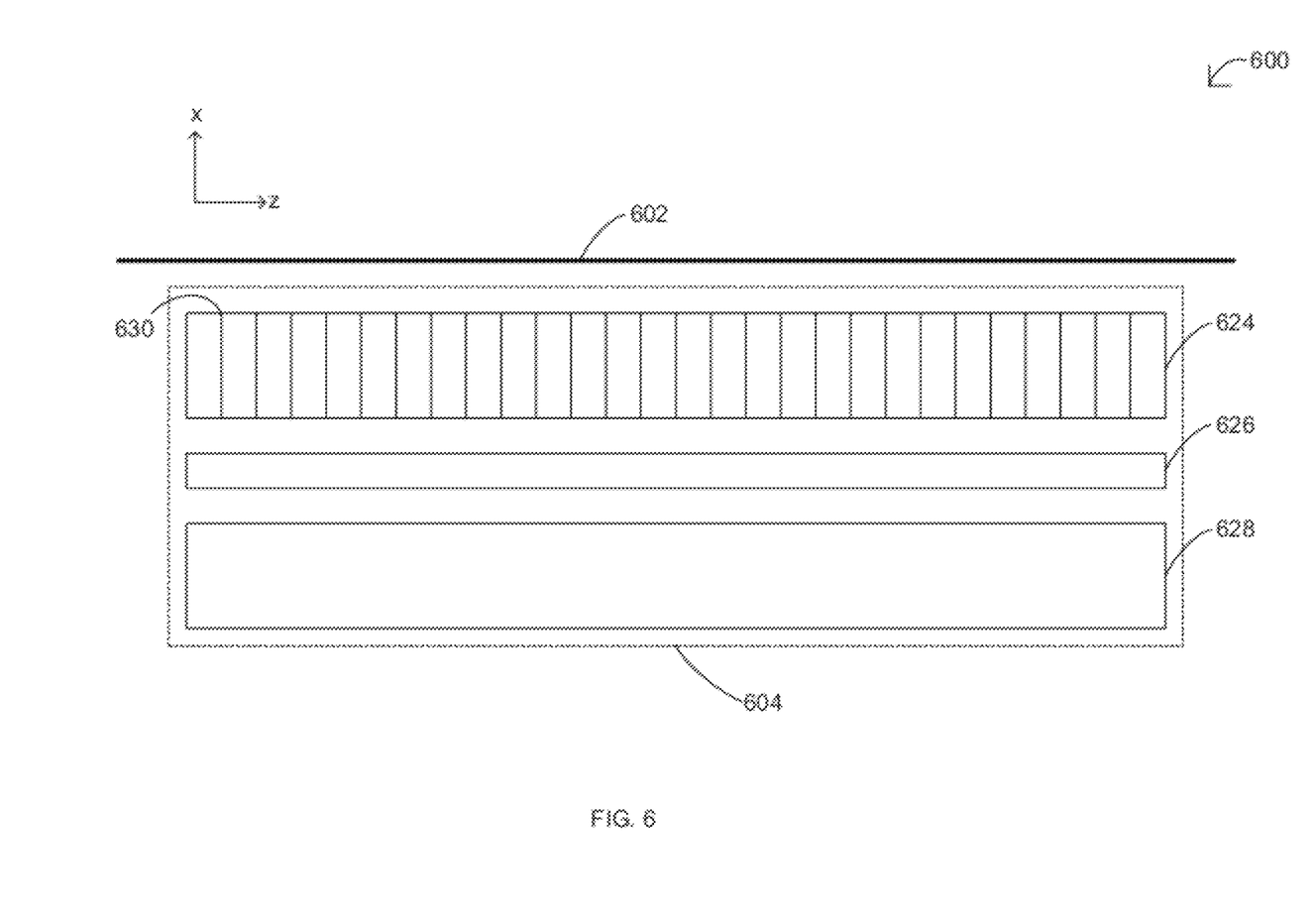
FIG. 6 illustrates an embodiment of a liquid chromatography detection unit of the present invention.

Yet another embodiment of a liquid chromatography unit of the present invention is illustrated in FIG. 6. The liquid chromatography unit 600 includes a fluid channel 602 and a gamma camera 604. In an embodiment, the fluid channel 602 comprises tubing, which may be arranged in a helix (not shown). 111 an embodiment, the fluid channel 602 comprises a separation column (not shown). The gamma camera 604 may be an Anger camera or some other suitable gamma camera. The gamma camera, 604 includes a collimator 624, a scintillator crystal 626, and an array of photomultiplier tubes 628. In an embodiment, the collimator 624 comprises lead with holes 630 arranged radially and orthogonally with respect to the fluid channel 602. In operation, some gamma rays from a non-positron emitting radioisotope or from a positron emitting isotope pass through the collimator 624 and impact the scintillator crystal 626, which produce photons that are imaged by the array of photomultiplier tubes 628.

Figure 7:
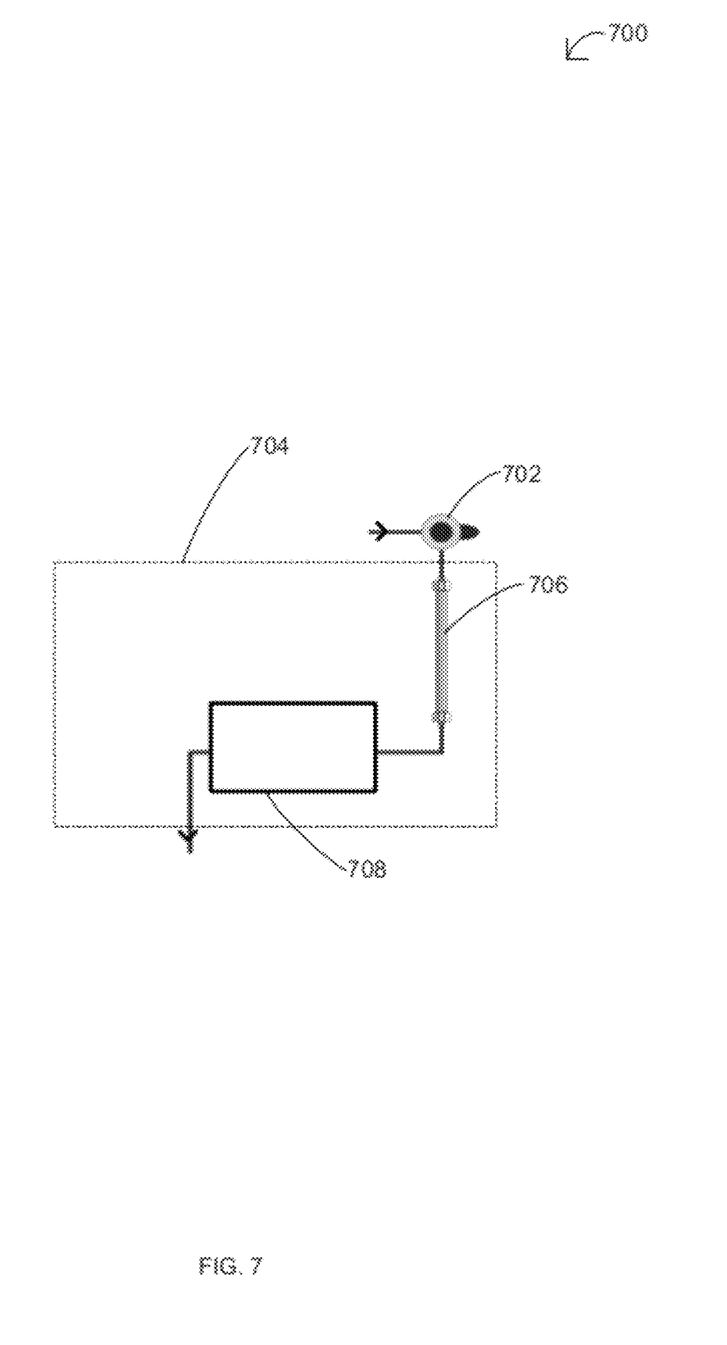
FIG. 7 illustrates an embodiment of a liquid chromatography system of the present invention.

An embodiment of a liquid chromatography system of the present invention is illustrated in FIG. 7. The system 700 includes an injector 702 and a liquid chromatography separation/detection arrangement 704. In an embodiment, the separation/detection arrangement 704 comprises a separation column 706 and a liquid chromatography detection unit 708. According to embodiments, the liquid chromatography detection unit comprises the detection unit 100 (FIG. 1), the detection unit 300 (FIG. 3), the detection unit 400 (FIG. 4), the detection unit 500 (FIG. 5), the detection unit 600 (FIG. 6), or another suitable detection unit. In another embodiment, the separation detection unit 704 comprises a detection unit that includes a separation column (e.g., the detection unit 500 of FIG. 5).

Figure 8:
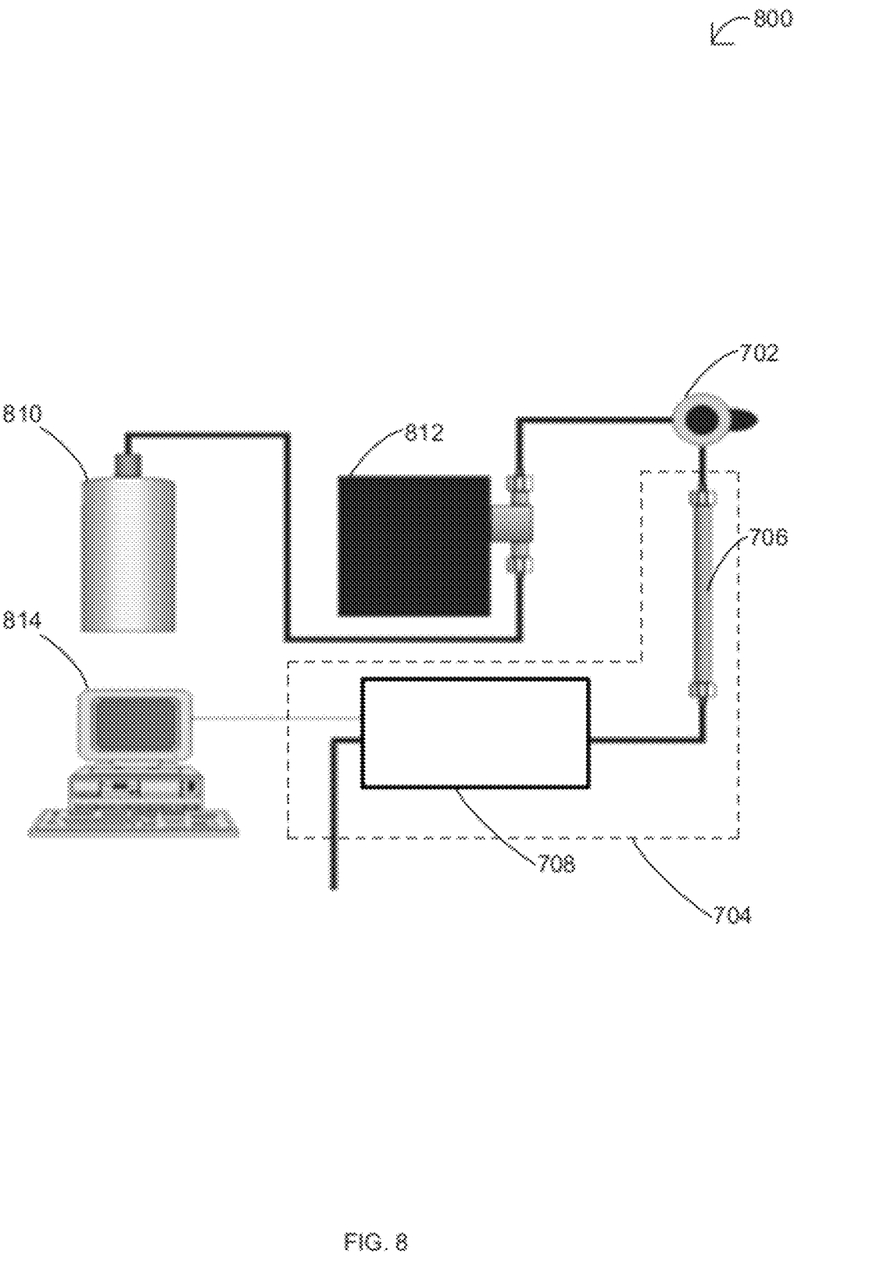
FIG. 8 illustrates an embodiment of a liquid chromatography system of the present invention.

Another embodiment of a liquid chromatography system of the present invention is illustrated in FIG. 8. The system 800 includes a reservoir 810, a pump 812, the injector 702, the liquid chromatography separation/detection arrangement 704, and a data system 814. In operation, the pump 812 pumps solvent from the reservoir 810 through the injector 702, the separation column 706, and the liquid chromatography detection unit 708. The injector 702 mixes a sample with a small amount of the solvent and injects this solution into the solvent stream. The sample includes a plurality of radiolabeled compounds. The solvent stream passes through the separation column 706 where the plurality of radiolabeled compounds are separated due to differences in their transport velocities within the separation column 706. The solvent stream then passes through the liquid chromatography detection unit 708 where distributions of radiation produced by each of the radiolabeled compounds is imaged as each radiolabeled compound passes through the detection unit 708. The data system 814 acquires image data from the detection unit 708 and analyzes the data to identify each radiolabeled compound (e.g., from the arrival time at the detection unit 708) as well as to determine concentrations of each radiolabeled compound.

Applications of the systems 700 and 800 (FIGS. 7 and 8) include biofuels development, biomedical research and therapies, and other biochemical applications.

DISCUSSION

A liquid chromatography detection unit of the present invention replaces a conventional radiation detector with one that has far greater sensitivity for positron-emitting isotopes but does not sacrifice the ability to separate peaks. The detection unit (e.g., the detection unit 300 or 400 of FIG. 3 or 4, respectively) is a parallel-plane PET camera. In an embodiment, each plane is 5 cm wide by 50 cm long, the planes are separated by 1 cm, and the tubing runs in the gap between the planes. The PET camera 304 may utilize conventional PET detector modules (e.g., detector modules 310 and 312) that are used in commercial PET cameras. As the length of tubing that is in the active detector area is considerably longer, the sensitivity for each "peak" of activity is greatly increased. The effective velocity for the radioactivity passing through the detection unit of the present invention can be slowed down by winding the tubing into a helix (e.g., the helix 420 of FIG. 4). The detection modules in the PET camera cover more solid angle and have higher gamma detection efficiency (2 cm thick of lutetium orthosilicate (LSO) compared to 1 cm thick of CsI:Tl for a conventional detector), which further increases the sensitivity. Finally, the system uses coincidence detection of individual gamma rays (as opposed to current mode readout), which has considerably better signal-to-noise ratio and dynamic range.

Unlike the conventional radiation detector, the proposed detector is able to measure the location of each radioactive decay, and so can image the "peak" as it moves through the fluid channel of the detection unit. A data acquisition system will essentially take a movie of the peak as it moves through the fluid channel, each frame of the movie is shifted (in space) so the centers of the peak are aligned, and the frames are then superimposed. This provides the efficiency of a large area detector without broadening the peaks. The performance estimation for the proposed detection unit additionally assumes that it is 50 cm long, that the detection unit can image the position of the positron annihilation with 4 mm accuracy, and that n turns of tubing are coiled in a 1 cm diameter helical spiral. In the limiting case of zero turns (a straight tube as shown in FIG. 3), each volume element of the liquid will spend 13.7 seconds in close contact with the detector, but the amount of time that is spent in front of each 4 mm tong resolution element (which is the amount that the detection unit blurs the width of the peak) is only 0.1 seconds, so the measured peak separation to width ratio is the intrinsic 6:1. For a coil with a non-trivial number of turns (n>50), the propagation velocity in the z-direction (FIG. 4) is approximately 58/n cm/sec. if a coil with a relatively coarse pitch (1 turn per cm) is used, each volume element of the liquid will spend 43 seconds in close contact with the detector, and the amount that the peak width is blurred (the amount of time that is spent in front of each 4 mm long resolution element) is only 0.3 seconds. The maximum pitch is ~7 turns per cm due to the outer diameter of the tubing, and with this pitch, each volume element spends 301 seconds (5 minutes) in the field of the camera and the peak is only broadened by 2.4 seconds—small compared to the 5 second intrinsic width of the peak and yielding a 5.4:1 peak separation to width ratio. This geometry is shown in FIG. 4.

Comparing the detection unit 400 (FIG. 4) to the $^{11}$C example of the background gives $f=\exp(-10/29.4)*[1-\exp(-5/29.4)]=0.11$, a 33-fold increase over the conventional system with 5 loops around the detector.

In an embodiment similar to the detection unit 500, the coiled tubing is replaced with two 25-cm long HPLC separation columns and the 50 cm long imaging detector is suitably located, which results in a much larger fraction of the radiotracer decaying in the field of the detector. If a $^{11}$C labeled compound is injected into the HPLC column at T=0, exits the column at $T_1$, and is in the field of the 50 cm detector during time $T_2$, then the fraction of the radiotracer that will decay in the field of the two subsequent 25 cm HPLC columns is given by $f=\exp(-T_1/29.4)*[1-\exp(-T_2/29.4)]$.

$T_1$ should be chosen sufficiently long for adequate separation of all compounds of interest. At T=0 all compounds overlap and have a width determined by the injection valve. Each compound is transported at a constant velocity that is characteristic of the compound. The width increases due to diffusion by a factor that is proportional to the square root of the time, and due to multiple flow paths by a factor that is proportional to the square root of the distance. Two different compounds are considered separated at time T1 when the difference in their velocities times $T_1$ exceeds the sum of their widths.

For two $^{11}$C labeled compounds that can be adequately separated in 5 minutes and have a column velocity of 2 cm/minute. $T_1$=5 minutes and $T_2$=25 minutes. In this case, the fraction of disintegrations that occur in the field of the camera is $f=\exp(-5/29.4)*[1-\exp(-25/29.4)]=0.48$. This is over a four-fold increase over the detection unit 400 and a 142-fold increase over the conventional system.

It is believed that the most efficient system would (1) use a column composition and solvent that separate all radioactive compounds present in the sample as soon as possible, (2) have a long enough column (or a sufficient number of columns coupled in series) so that almost all the radioactive disintegrations occur in the column, and (3) use a detection system with a large solid angle of coverage that can image the full length of the column or at least that portion of the column where distributions have sufficiently separated.

EXAMPLE

Figure 9:
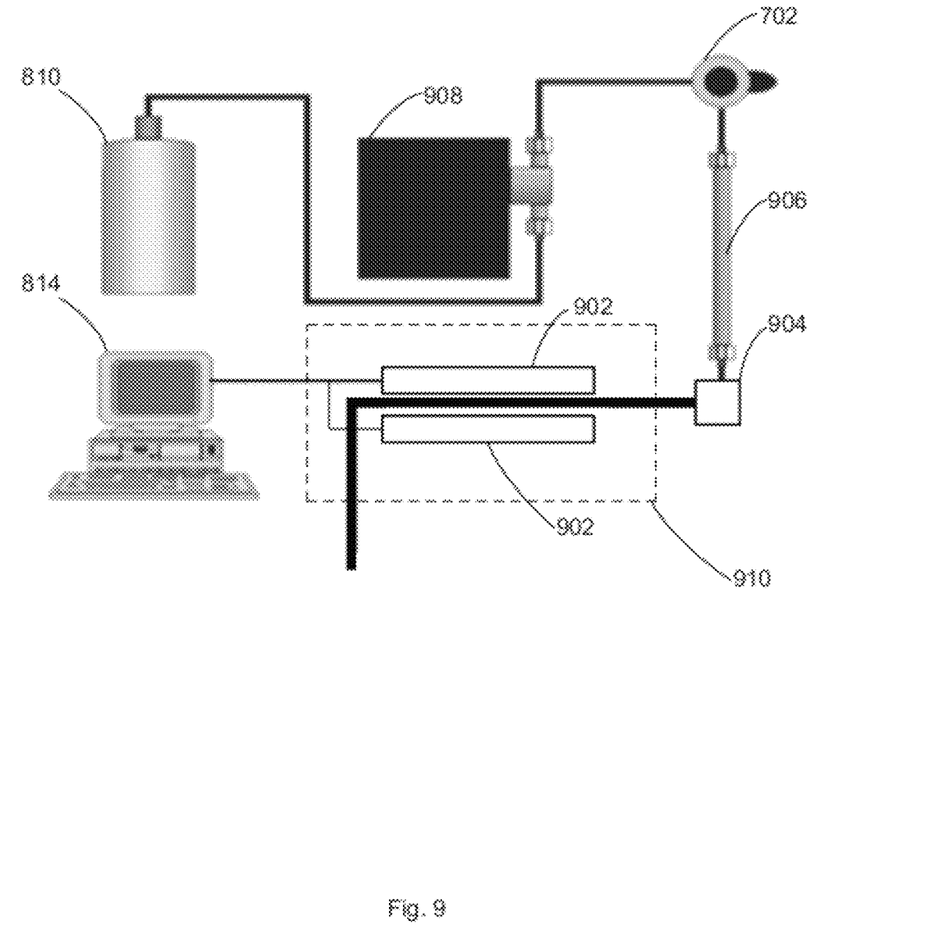
FIG. 9 illustrates an experimental setup of a liquid chromatography system in accordance with an example of the present invention.

A study of a high-sensitivity HPLC radiation detector. The experimental setup of the HPLC system and detectors is shown in FIG. 9. For this study, 8 HR+PET detector modules 902 were assembled into 2 parallel planes with a 0.75 mm inner diameter tube running along the 1.5 cm gap between the detector planes. The HR+ detector modules 902 also had a 1.5 cm gap between the active faces (since the HR+ module housing was wider at the base than the active front face), so the HR+ module assembly is 18.5 cm (along the tube). The HR+ detector planes were readout using separate HRRT detector head interface acquisition boards, in order to acquire coincident events between all HR+ crystals in opposing detector planes. This high-sensitivity radiation detector was placed line after a conventional radiation detector 904 to allow a direct comparison of measurements.

The HPLC was performed using a Phenomenex Luna 5µ C18(2) column 906 (250 mm×4.60 mm) with 85:15:0.5 (v/v) CH3OH:H2O:acetic acid as the mobile phase solvent. The flow rate of 1 mL/min was controlled by a Waters model 6000A pump 908. The eluent was monitored for radioactivity using both the conventional radiation detector 904 (i.e., a Carroll and Ramsey Associates Model 105S detector with a 1 cm3 CsI(Tl) crystal probe sitting directly on the unlooped tube) and high-sensitivity HR+ radiation detectors 902 (i.e. PET camera 910).

Figure 10:
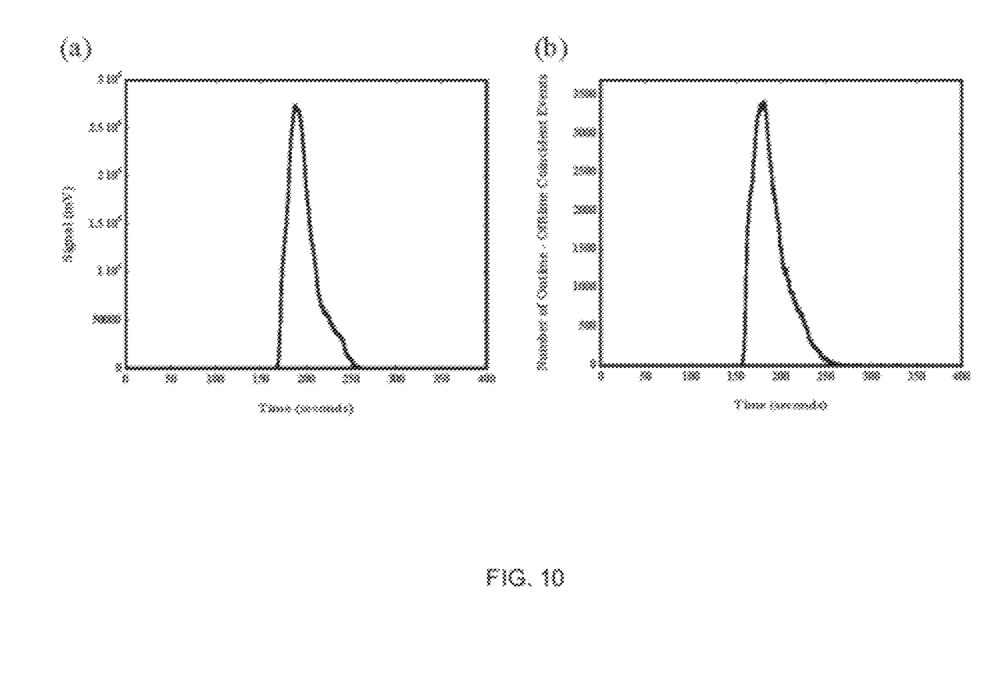
FIG. 10a provides the HPLC signal from a conventional radiation detector.
FIG. 10b provides the HPLC signal from a HR+ radiation detector in accordance with an example of the present invention. Both are plotted with 1 sec time bins.

FIG. 10 shows the radioactivity measured by both radiation detectors when 381 µCi of [$^{11}$C]carfentanil was injected into the HPLC system. For this relatively large signal, a single peak with nearly identical shapes from both radiation detectors (with very little noise) was observed.

Figure 11:
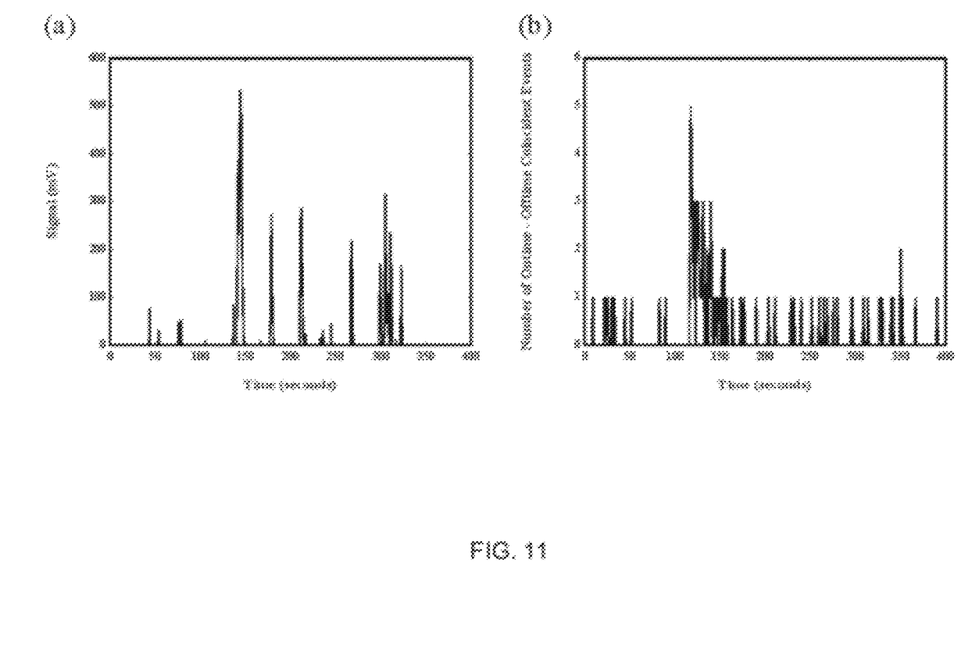
FIG. 11a provides the HPLC signal from a conventional radiation detector.
FIG. 11b provides the HPLC signal from a HR+ radiation detector in accordance with an example of the present invention. Both are plotted with 1 sec time bins.

FIG. 11 shows the radioactivity measured by both detectors when 2.5 µCi of the same radioactive compound was injected. The signal-to-noise ratio for the HR+ detector signal is 5:1, assuming a 100 sec peak width (from FIG. 10b). In contrast, it is difficult to even determine the number of peaks for the conventional radiation detector at this low level of radioactivity. It is also difficult to estimate the noise for the conventional radiation detector at low levels of radioactivity, since the noise is not Poisson and the character of the noise appears to be variable.

Figure 12:
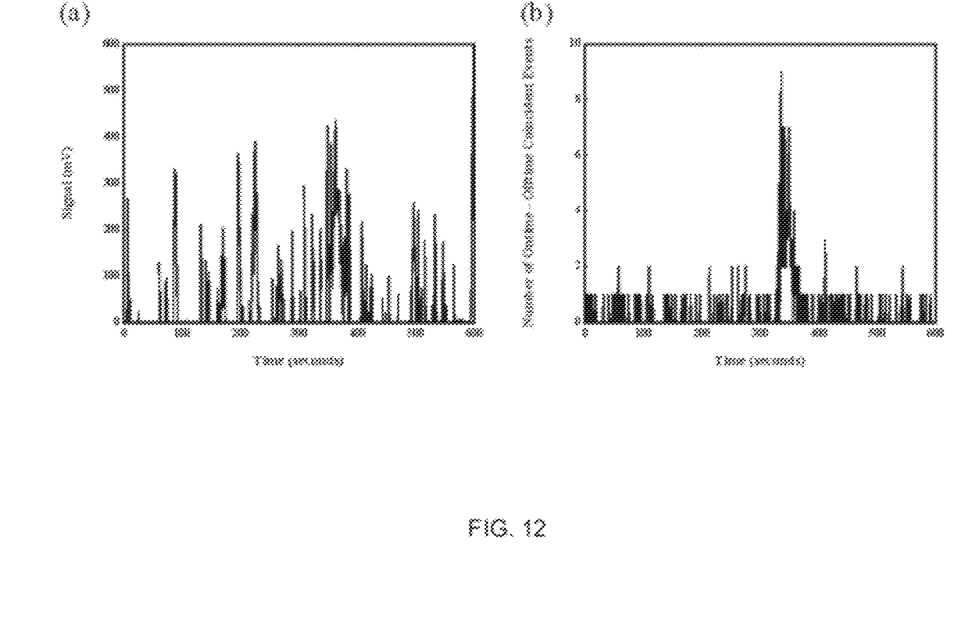
FIG. 12a provides the HPLC signal from a conventional radiation detector.
FIG. 12b provides the signal from a HR+ radiation detector in accordance with an example of the present invention. Both are plotted with 1 sec time bins.

FIG. 12 shows similar results when about 1 µCi of [$^{11}$C] methyl iodide was injected into the HPLC system (with a single narrower peak). We measure a signal-to-noise ratio of 14:1 with the HR+ detector (FIG. 12b), but a corresponding signal with the conventional radiation detector was not detected (FIG. 12a).

As used herein and in the appended claims, the singular forms "a", "and", and "the" include plural referents unless the context clearly dictates otherwise. The foregoing detailed description of the present invention is provided for the purposes of illustration and is not intended to be exhaustive or to limit the invention to the embodiments disclosed. Accordingly, the scope of the present invention is defined by the appended claims.

What is claimed is:

1. A liquid chromatography detection unit comprising:
   a fluid channel;
   a position sensitive radiation detector positioned along a length of the fluid channel, the position sensitive radiation detector operable to acquire images of a distribution of a radiolabeled compound as the distribution travels along the length of the fluid channel over a period of time; and
   a data acquisition unit operable to combine the images of the distribution that are obtained over the period of time.

2. The liquid chromatography detection unit of claim 1 wherein the fluid channel comprises tubing.

3. The liquid chromatography detection unit of claim 2 wherein the tubing is arranged in a helix.

4. The liquid chromatography detection unit of claim 2 wherein the tubing is positioned along a substantially straight line.

5. The liquid chromatography detection unit of claim 1 wherein the fluid channel comprises a separation column.

6. The liquid chromatography detection unit of claim 1 wherein the position sensitive radiation detector comprises a positron emission tomography camera.

7. The liquid chromatography detection unit of claim 6 wherein the positron emission tomography camera comprises a first positron emission tomography detector with a first detection surface facing a second detection surface of a second positron emission tomography detector.

8. The liquid chromatography detection unit of claim 7 wherein the length of the fluid channel is parallel to the first and second detection surfaces.

9. The liquid chromatography detection unit of claim 7 wherein the first positron emission tomography detector and the second positron emission tomography detector are each 5 centimeters wide by 50 centimeters long.

10. The liquid chromatography detection unit of claim 7 wherein the first detection surface and the second detection surface are separated by 1 centimeter.

11. The liquid chromatography detection unit of claim 6 wherein the positron emission tomography camera includes positron emission tomography detector modules.

12. The liquid chromatography detection unit of claim 1 wherein the position sensitive radiation detector comprises a gamma camera.

13. The liquid chromatography detection unit of claim 1 wherein the length of the fluid channel is 50 centimeters.

14. The liquid chromatography detection unit of claim 1 wherein the data acquisition unit is further operable to determine a concentration of the radiolabeled compound using the combined images.

* * * * *